United States Patent
Dan-Jumbo (10) Patent No.: US 9,518,907 B2
(45) Date of Patent: Dec. 13, 2016

(54) METHODS AND APPARATUS TO DETERMINE INTEGRITY OF COMPOSITE STRUCTURES

(71) Applicant: The Boeing Company, Chicago, IL (US)

(72) Inventor: Eugene A. Dan-Jumbo, Bothell, WA (US)

(73) Assignee: THE BOEING COMPANY, Chicago, IL (US)

( * ) Notice: Subject to any disclaimer, the term of this patent is extended or adjusted under 35 U.S.C. 154(b) by 224 days.

(21) Appl. No.: 14/157,211

(22) Filed: Jan. 16, 2014

(65) Prior Publication Data

US 2015/0198514 A1    Jul. 16, 2015

(51) Int. Cl.
| | |
|---|---|
| G01N 19/04 | (2006.01) |
| G01N 13/02 | (2006.01) |
| B64C 1/12 | (2006.01) |
| B64C 3/26 | (2006.01) |
| G01M 5/00 | (2006.01) |
| B64C 1/00 | (2006.01) |

(52) U.S. Cl.
CPC ............... *G01N 13/02* (2013.01); *B64C 1/12* (2013.01); *B64C 3/26* (2013.01); *G01M 5/0016* (2013.01); *B64C 2001/0072* (2013.01); *G01N 2013/0208* (2013.01)

(58) Field of Classification Search
CPC ............... G01N 13/02; B64C 1/12; B64C 3/26
USPC ........................................ 73/150 A
See application file for complete search history.

(56) References Cited

U.S. PATENT DOCUMENTS

| | | | |
|---|---|---|---|
| 5,216,799 | A | 6/1993 | Charnock et al. |
| 8,386,194 | B1 | 2/2013 | Baldwin et al. |
| 8,409,384 | B2 | 4/2013 | Dan-Jumbo et al. |
| 8,449,703 | B2 | 5/2013 | Dan-Jumbo et al. |
| 8,524,356 | B1 | 9/2013 | Dan-Jumbo et al. |
| 8,540,909 | B2 | 9/2013 | Dan-Jumbo et al. |
| 8,616,050 | B1 | 12/2013 | Dan-Jumbo et al. |
| 8,617,694 | B1 | 12/2013 | Dan-Jumbo et al. |
| 2013/0260077 | A1 | 10/2013 | Dan-Jumbo et al. |
| 2013/0337214 | A1 | 12/2013 | Dan-Jumbo et al. |

FOREIGN PATENT DOCUMENTS

| | | |
|---|---|---|
| CA | 2859212 | 7/2015 |
| EP | 2869954 | 7/2015 |

OTHER PUBLICATIONS

European Patent Office, "Extended European Search Report," issued in connection with European Patent Application No. 14197566.4, issued on Jun. 12, 2015, 12 pages.

(Continued)

*Primary Examiner* — John Fitzgerald
*Assistant Examiner* — Rodney T Frank
(74) *Attorney, Agent, or Firm* — Hanley, Flight & Zimmerman, LLC (57) ABSTRACT

Apparatus and methods to determine structural integrity of composites are described herein. One described example method for determining sufficiency of structural integration of a composite structure for an aircraft includes applying a fluid droplet to a surface of the composite structure, determining a three-dimensional contact angle between the surface and a portion of the droplet, comparing the three-dimensional contact angle to a threshold angle, and determining whether the structural integration of the composite structure is sufficient based on the comparison.

20 Claims, 8 Drawing Sheets

(56) References Cited

OTHER PUBLICATIONS

Durkee, "Using Simple Science to Assay Surface Cleanliness," Cleaningtimes, www.metalfinishing.com, Feb. 2008, 4 pages.
Encinas et al., "Surface modification of aircraft used composites for adhesive bonding," International Journal of Adhesion & Adhesives, vol. 50, 2014, 8 pages.
Yuan et al., "Contact Angle and Wetting Properties," Surface Science Techniques, Jan. 1, 2013, Springer Berlin Heidelberg, 34 pages.
Canadian Intellectual Property Office, "Examiner's Report", issued in connection with Canadian Patent Application No. 2,859,212, issued on Oct. 26, 2015, 5 pages.
Roger P. Woodward, "Prediction of Adhesion and Wetting from Lewis Acid Base Measurements", First Ten Angstroms, Inc, 2000, downloaded from [http://www.firsttenangstroms.com/pdfdocs/TPOsinAutomotive2000.pdf], retrieved on Dec. 7, 2015, 6 pages.
Canadian Patent Office, "Examiner's Report", issued in connection with Canadian Patent Application No. 2,859,212, issued on Jun. 10, 2016, 3 pages.

METHODS AND APPARATUS TO DETERMINE INTEGRITY OF COMPOSITE STRUCTURES

FIELD OF THE DISCLOSURE

This patent relates generally to composites and, more particularly, to methods and apparatus to determine integrity of composite structures.

BACKGROUND

Composite structures used in vehicles (e.g., aircraft, automobiles, space craft, missiles, etc.) may be composed of a skin layer and a support layer (e.g., a stringer layer in an aircraft). In load-bearing applications, the skin layer and the support layer are commonly coupled via fasteners instead of or in addition to adhesive due to uncertainty in the sufficiency of structural integration between adhered layers. Use of fasteners to couple the layers of composite structures in vehicles may add significant weight and/or negatively impact aerodynamic characteristics (e.g., increase drag). Additionally, use of fasteners in composite structures may require significant manufacturing cost (i.e., time, parts and labor).

SUMMARY

The present disclosure provides an exemplary method for determining the sufficiency of structural integration of a composite structure for an aircraft, which includes applying a fluid droplet to a surface of the composite structure, determining a three-dimensional contact angle between the surface and a portion of the droplet, comparing the three-dimensional contact angle to a threshold angle, and determining whether the structural integration of the composite structure is sufficient based on the comparison.

According to another aspect of the present disclosure, an improved aircraft component is provide that requires fewer fasteners. The aircraft component includes an external skin having a bonded composite structure defining a skin surface area of an aircraft, a support frame, and an adhesive applied to the composite structure to attach the external skin to the support frame. The composite structure has sufficient structural integration to enable adhesive attachment of the external skin to the support with less than, on average, 0.50 fasteners to couple the skin and the frame per square-foot of the skin surface area, where a three-dimensional contact angle between the composite structure and a portion of a fluid droplet applied to the surface of the composite structure is less than a predetermined threshold angle of about 10 degrees.

According to another aspect of the present disclosure, an example tangible machine readable medium is described that has instructions stored thereon, which when executed, cause a machine to calculate a three-dimensional contact angle of a droplet placed onto a surface of a composite structure based on a measured diameter and volume of the droplet, and compare the three-dimensional contact angle to a threshold angle. A three-dimensional contact angle less than the threshold angle indicates sufficient structural integration of the composite structure. A three-dimensional contact angle greater than the threshold angle indicates insufficient structural integration of the composite structure. The instructions, when executed, also cause the machine to output whether the composite structure has sufficient structural integration.

Wherever possible, the same reference numbers will be used throughout the drawing(s) and accompanying written description to refer to the same or like parts. As used in this disclosure, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

Methods and apparatus to eliminate or greatly reduce the number of fasteners coupling adhered layers of a load-bearing composite structure are described herein. The examples described herein allow reduction of weight, complexity, cost, manufacturing time, and associated repair/warranty costs in comparison to composite structures that rely primarily on fasteners to hold together the layers of the composite structures. Composite structures are generally composed of two or more materials (e.g., layers, etc.) coupled together via fasteners and/or adhesive. The use of adhesive alone to couple the layers may result in uncertainty as to whether the layers have sufficient structural integration. For example, the layers may not be sufficiently bonded to one another to enable the composite structure to be used in load-bearing applications. Contaminants such as, for example, fluorine may decrease the structural integration of the layers. In load-bearing applications (e.g., aircraft or other vehicles), uncertainty of structural integration may necessitate additional or extensive use of mechanical fasteners (e.g., screws, rivets, etc.) to ensure sufficient overall strength and/or coupling of the composite structure layers. The use of fasteners may significantly increase the weight of a composite structure, particularly in applications in which the fasteners are spaced at close intervals to ensure sufficient strength of the composite structure. Additionally, the use of fasteners often requires significant assembly time, part cost, and/or effort during manufacturing.

Determining sufficiency of structural integration of each composite structure prior to assembly enables these composite structures to have relatively few or no fasteners and to be used in load-bearing applications such as, for example, aircraft or other vehicles. In an aircraft, for example, determining sufficiency of structural integration of the composite structure layers prior to their assembly into the aircraft enables use of bonded (e.g., adhered) external outboard composite structures (e.g., wings, fins, struts, etc.) having few or no fasteners holding together the layers of the composite structures. Wing structures, for example, may have adhesive coupling or attaching an external skin to a support structure (e.g., a stringer) with few or no fasteners. Testing the structural integration of the adhered layers for each wing structure, for example, may be used to approve each wing structure or any other appropriate structural composite individually for sufficient strength and, thus, acceptance for final assembly integration.

In accordance with the teachings of this disclosure, an example method may be used to determine sufficiency of structural integration of adhered or bonded layers of composite structures prior to use and/or assembly of these composite structures into a final assembly. This determination allows use and/or approval of individual bonded composite structures having few or no fasteners for use in load-bearing applications. To make such a determination, a dynamic droplet ballistically deposited onto a surface of a composite structure being evaluated may be applied by a pipette, for example. A three-dimensional contact angle of the droplet, which is an angle between a three-dimensional vector of a surface loft of the dynamic fluid droplet and the surface of the composite structure, indicates surface tension of the composite structure. In other words, the vector has components in three dimensions relative to the surface of the composite structure. Alternatively, the contact angle may be defined by a two-dimensional cross-sectional measurement of the droplet. The three-dimensional contact angle may be determined and compared to a threshold angle that may be based on corresponding strength requirements, for example. The sufficiency of the structural integration of the composite structure may be indicated by the comparison. For example, if the three-dimensional contact angle is less than the threshold angle, there is sufficient structural integration of the composite structure. The three-dimensional contact angle of the droplet may be measured and/or calculated by, for example, measuring a volume and/or a diameter of the droplet deposited onto the surface of the composite structure.

As described in greater detail below, determination of a three-dimensional droplet contact angle on composite structures enables the evaluation of the sufficiency of structural integration of each composite structure prior to final assembly. In the example of an aircraft, an external skin having a bonded composite structure may be adhered to a support frame to define a load-bearing composite structure, where the composite structure of the external skin may be structurally verified via a droplet. This verification may allow the composite structure to have few or no fasteners coupling the composite layers together. Composite structures, in some examples, are tested prior to final assembly integration. Thus, composite structures determined to have insufficient structural integration may be reworked and/or rejected prior to final assembly, thereby preventing the composite structure with insufficient structural integration from being assembled. As a result, savings on potential repairs and/or reworking after assembly of composite structures with insufficient structural integration may be realized. Additionally or alternatively, the test droplet may be used to quantitatively determine the strength of the composite structure (e.g., a numerical value based on a measured or calculated three-dimensional droplet contact angle).

Using the examples described herein enables load-bearing composite structures of an external skin that is bonded to a frame to have less than, on average, 0.50 fasteners to couple the composite layers per square-foot of skin surface area. In some examples, the composite structure may be integrated into the final assembly with only adhesive bonding the composite structure to the support frame. In the example of a bonded wing composite structure, a reduction of the number of fasteners used to couple the composite structure and support frame together may result in a corresponding weight reduction of 60-70% in comparison to a known wing assembly. Additionally, the reduction of the number of fasteners used may also improve aerodynamic factors such as drag coefficient for composite structures used in aerodynamic applications (e.g., wings, etc.) by significantly increasing smoothness (e.g., surface flatness) of the skin surface.

Figure 1:
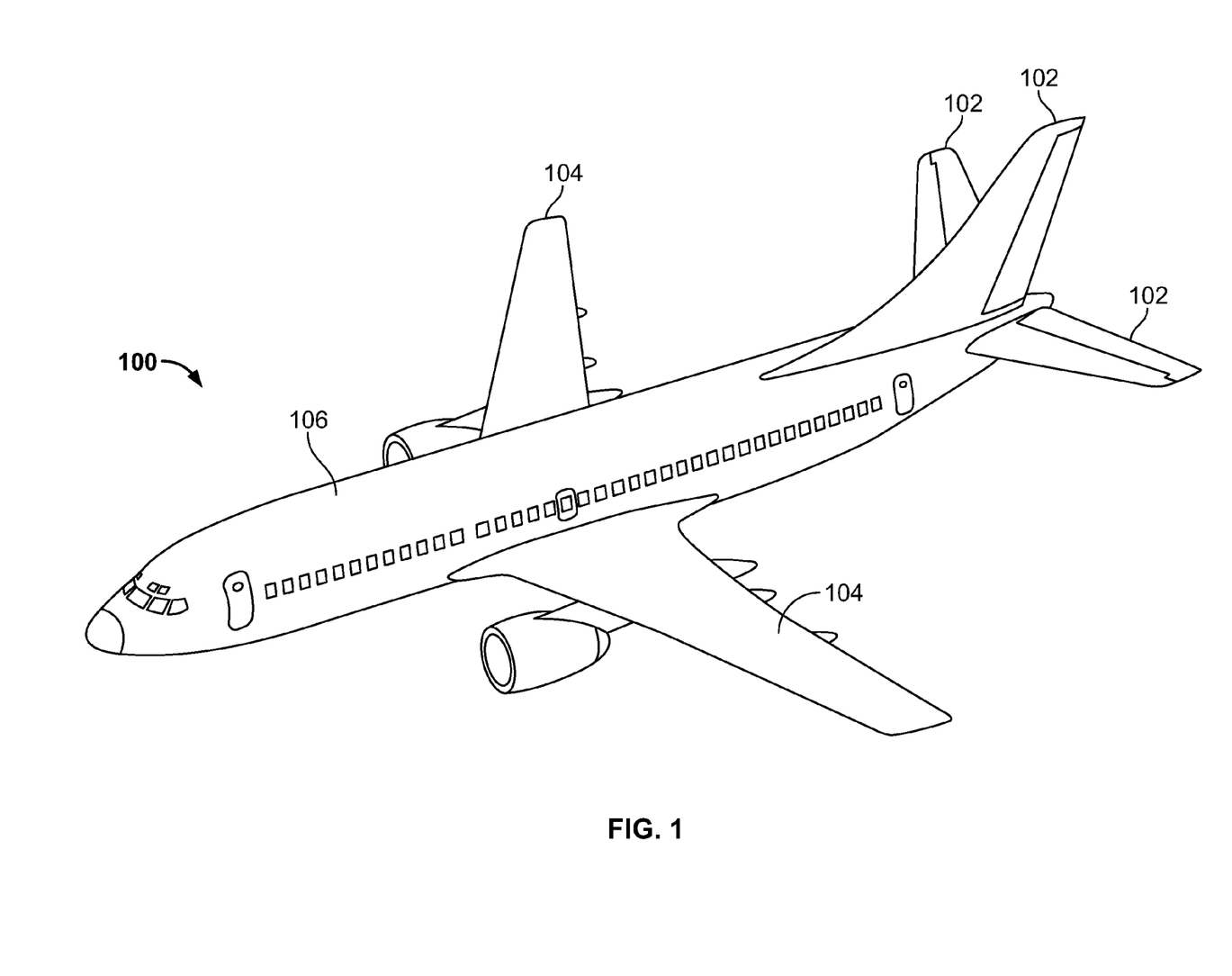
FIG. 1 illustrates an example aircraft in which the examples disclosed herein can be implemented.

FIG. 1 illustrates an example aircraft 100 having stabilizers 102 and wings 104 attached to a fuselage 106 in which the examples described herein can be implemented. The examples described herein may be applied to any of the stabilizers 102, the wings 104 and/or any other exterior or outboard structure (e.g., a horizontal stabilizer, a wing strut, an engine strut, a canard stabilizer, etc.) of the fuselage 106. For example, the wings 104 and/or the stabilizers 102 may have an external skin made of a composite structure in which a bonding surface may be adhered to an internal support frame. As mentioned above, an adhered composite structure may allow significant weight savings compared to a composite structure relying primarily on fasteners for structural integration. While an aircraft is depicted, the examples described may be applied to any vehicle or any other scenario where load-bearing composite structures are used.

Figure 2:
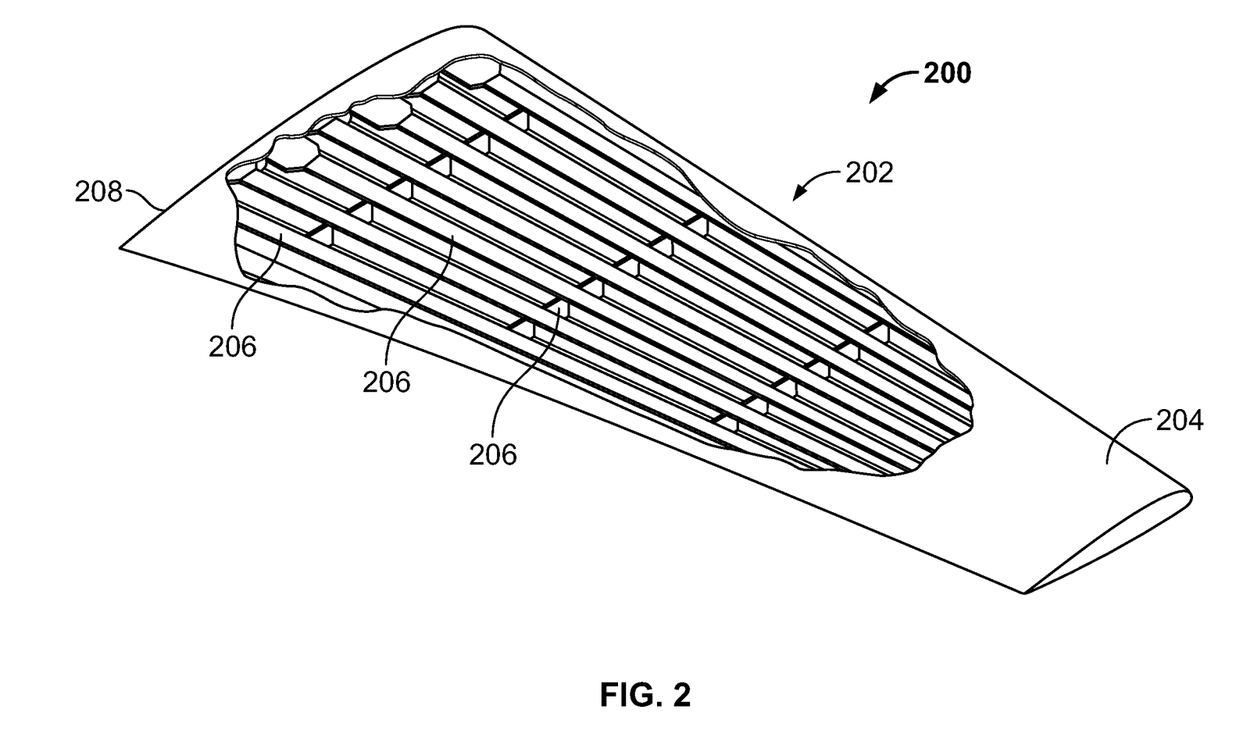
FIG. 2 is a cutaway view of an example aircraft wing having a composite structure in which the examples disclosed herein can be implemented.

FIG. 2 is a cutaway view of an example aircraft wing 200 with a composite structure 202 in which the examples described herein can be implemented. An external skin 204 includes a bonded composite structure 202, which is coupled to and surrounds stringers 206 (e.g., a support frame), which are arranged in a pattern to support the composite structure 202. While the stringers 206 are shown in a regular pattern with corresponding cross-beams, they may be arranged in an irregularly spaced pattern, or angled pattern, etc. Typically, to provide sufficient structural rigidity to withstand operational loads encountered by the wing 200, the stringers 206 are coupled to the external skin 204 via numerous fasteners. These fasteners are usually spaced at relatively close intervals to ensure sufficient coupling between the external skin 204 and the stringers 206, thereby allowing the composite structure 202 to have sufficient overall mechanical strength. However, in the example of FIG. 2, the composite structure 202 forming the external skin 204 has a sufficient structural integration (or intermolecular dynamic forces) to enable the external skin 204 to be coupled to the stringers 206 primarily by adhesive instead of fasteners and, thus, provides a significant reduction in weight (e.g., a 60-70% weight reduction in the structure). The composite structure 202 preferably has sufficient structural integration to enable adhesive attachment of the external skin to the support frame, with less than 0.50 fasteners per square-foot of the skin surface area, when a three-dimensional contact angle between a surface of the composite structure and a portion of a fluid droplet applied to the surface of the composite structure is less than a pre-determined threshold angle. Additionally, the reduction in the number of fasteners may also allow greater aerodynamic performance by reducing aerodynamic skin friction caused by the fasteners. This reduction in the number of fasteners or elimination thereof may also allow savings in part costs, manufacturing time, labor, etc.

Formation of the composite structure, in some cases, may result in partial or insufficient structural integration of the composite structure, which may be due to contamination in bonding surfaces of the composite structure. Verification of the composite structure prior to final assembly (e.g., integration) may prevent composite structures with insufficient structural integration and load bearing strength from being assembled, thereby reducing and/or eliminating rework or repair efforts. For example, verification may occur prior to an attachment portion 208 of the wing 200 being integrated onto a fuselage of an aircraft 201 by, for example, use of fasteners, bonding, or any other appropriate attachment method. Verification prior to a composite structure being integrated into a main or final assembly of vehicles (e.g., aircraft, automobile, etc.) may allow the load-bearing composite structures of the vehicles to have fewer than 0.50, on average, fasteners coupling a skin and a frame per square-foot of surface area defined by the skin.

Figure 3A:
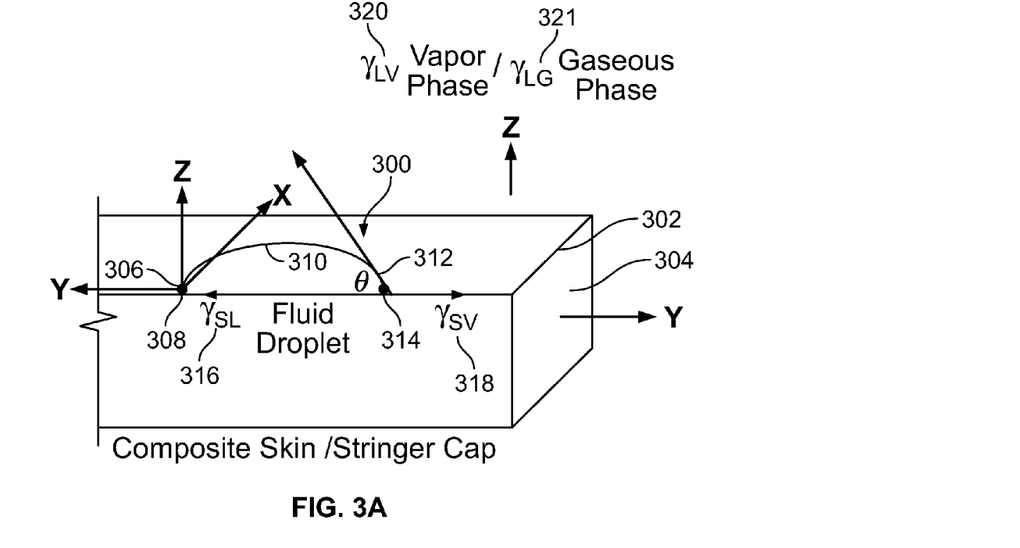
FIG. 3A is a view of an overall loft of a dynamic droplet on a composite surface in accordance with the teachings of this disclosure.

FIG. 3A is a view of an overall loft (i.e., geometry) of a dynamic droplet 300 on a composite skin surface 302 of a composite structure 304 in accordance with the teachings of this disclosure. A coordinate axis 306 depicts three dimensional axes. The droplet 300 is used to determine whether the composite structure 304 has sufficient structural integration of the composite layers. The droplet 300 is applied (e.g., deposited) onto the composite skin surface 302, which may occur through a pipette or any other appropriate means of deposition. The volume of the droplet 300 may be measured as the droplet 300 is being deposited or may be based on a known amount of liquid applied.

The geometry of the droplet 300 indicates the degree of structural integration of the composite structure 304. The droplet 300 includes a head 308, a center 310 and a tail 312. The tail 312 defines a three-dimensional contact angle 314, which is denoted by the symbol θ, between a vector of a three-dimensional loft of the tail 302 and the surface 302. The three-dimensional contact angle 314 is a dynamic angle that can be used to determine the intermolecular forces in the composite structure 304 and/or the margin of safety (e.g., factor of safety) of the composite structure 304. Alternatively, the three-dimensional contact angle 314 may be defined by a two-dimensional cross-sectional measurement of the droplet 300. The droplet 300 has surface tension force vectors corresponding to different forces acting on the droplet 300. A solid liquid tension force vector 316, which is depicted by the symbol $\gamma_{SL}$, indicates the tension force between the surface 302 and the droplet 300. $\gamma_{SL}$ is the interfacial surface tension force of the droplet 300 on the skin 302. A solid vapor tension force vector 318, which is depicted by the symbol $\gamma_{SV}$, indicates the surface tension force between the surface 302 and a vapor component of the droplet 300. Tension force vectors 320, 321 depicted by $\gamma_{LV}$ and $\gamma_{LG}$, respectively, indicate liquid vapor and liquid gas forces. $\gamma_{LG}$ is the surface tension force of the surface 302 due to the droplet 300 being in equilibrium with the gaseous phase of the fluid droplet 300. Equation 1 below, which is a modified Young's equation developed by The Boeing Company, includes the gaseous phase, $\gamma_{LG}$, to account for the hydrophilic portion to calculate a surface tension force between a composite structure and a droplet.

$$\gamma_{SV} = \gamma_S - \pi_S = \gamma_{LV} \cos \theta \gamma_{SL} + \gamma_{LG} \quad (1)$$

$\pi_S$ is a term denoting the equilibrium spreading pressure of the droplet 300 deposited on the composite surface 302. While Equation 1 shows a specific example relationship of the aforementioned tension forces, other equations may be used to relate the surface tension forces and/or three-dimensional contact angle.

Figure 3B:
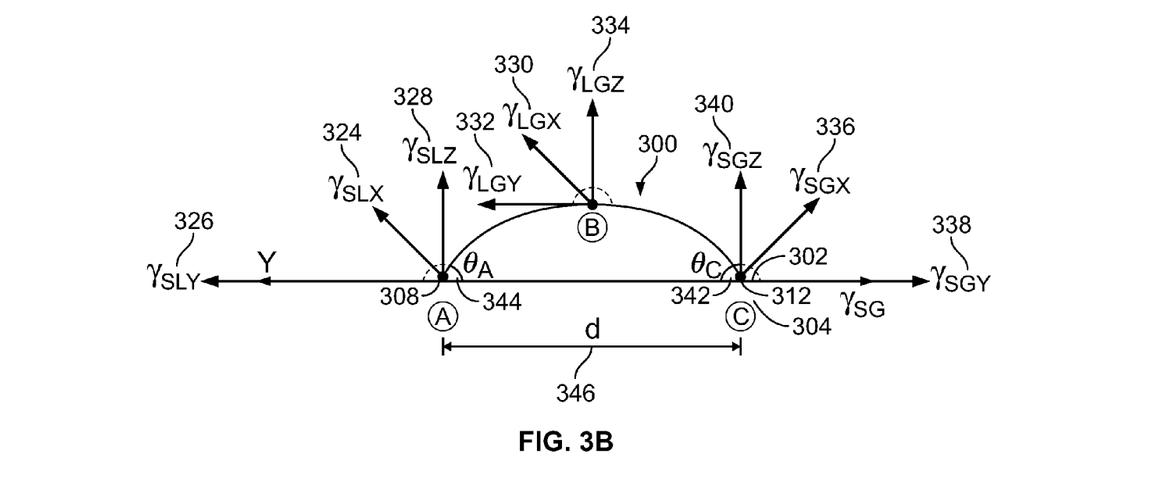
FIG. 3B is a cross-sectional view of the droplet of FIG. 3A.

FIG. 3B is a cross-sectional view of the droplet 300 of FIG. 3A. This view depicts nine degrees of freedom of the fluid droplet 300. Directional vector components 324, 326, 328 of the solid liquid tension force vector 316, depicted by $\gamma_{SL}$, correspond to the directions x, y and z, respectively, indicated by the coordinate axis 306. Directional vector components 330, 332, 334 of the liquid gas tension force vector 316, depicted by the symbol $\gamma_{LG}$, correspond to the directions x, y and z, respectively, indicated by the coordinate system 306. Directional vector components 336, 338, 340 of the solid gas tension force vector 316, which is depicted by the symbol $\gamma_{SG}$, also correspond to the directions x, y and z, respectively. A three-dimensional contact angle 342, depicted by the symbol, $\theta_c$, is the three-dimensional angle at the tail 312 of the droplet 300 that may be compared to a threshold angle to determine sufficiency of mechanical integration in the composite structure 304. In some examples, the threshold angle being less than approximately 10 degrees indicates sufficient mechanical integration. The three-dimensional contact angle 342 is greater than a three-dimensional contact angle 344 at the head 308 of the droplet 300. This difference between the three-dimensional contact angles 342, 344 is due to the geometric and/or rotational perturbation of the droplet 300 on the surface 302. Use of Equation 2 (i.e., the Bikerman equation) allows a diameter 346, which is denoted by d, the aforementioned droplet 300 volume, which is denoted by V, and the three-dimensional contact angle 344, which is denoted by $\theta_c$, to be related to one another.

$$\frac{d^3}{V} = \frac{24\sin^3\theta_C}{\pi(2 - 3\cos\theta_C + \cos^3\theta_C)} \quad (2)$$

Equation 2 may be used, for example, to calculate the three-dimensional contact angle 344 based on the diameter 346 and a known volume of the droplet 300. Conversely, the three-dimensional contact angle 344 may be used to calculate a diameter or a droplet volume. Equations 1 and 2 are only example calculations that may be used to relate any combination of variables including, but not limited to, three-dimensional contact angle, threshold angle, fluid drop diameter, fluid drop volume and/or stress criteria, etc. Other equations and/or relations may be used to relate the aforementioned variables to sufficient structural integration of composite structures.

In some examples, a threshold angle may be determined by modeling a deposition of a simulated fluid droplet onto a faying surface of a bonded composite structure. Force components at the head and tail of the simulated droplet and/or a surface tension force between the composite structure and the simulated droplet may be resolved using, for example, a requisite bonded strength of the composite structure corresponding to an operational force requirement. This determination may be made using a modified Young's equation such as, for example, Equation 1. The threshold angle may be calculated by using any combination of, but not limited to, stress criteria of the composite structure, operational loads, type of droplet, droplet test conditions, a modified Young's equation such as Equation 1, the Bikerman equation (i.e., Equation 2), etc. Additionally or alternatively, empirical methods may be used to determine the threshold angle. For example, threshold droplet contact angles may be measured and/or calculated in conjunction with Equation 2 based on a three-dimensional contact angle of a droplet deposited onto a known composite structure (e.g., already determined to meet requisite strength criteria).

Figure 4:
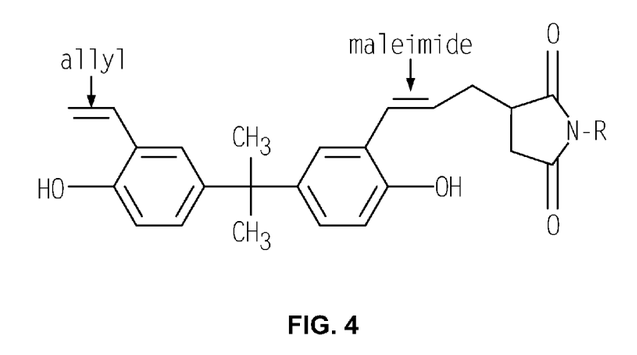
FIG. 4 illustrates an example molecular structure of a typical composite skin.

FIG. 4 illustrates an example molecular structure of a typical composite skin. While a bismaleimide structure is shown, any appropriate composite molecular structure may be used such as epoxy, polyamide, thermoplastic, etc. The mechanical structure exhibits typical C—C (carbon carbon) double bonds seen in composite structural materials.

Figure 5:
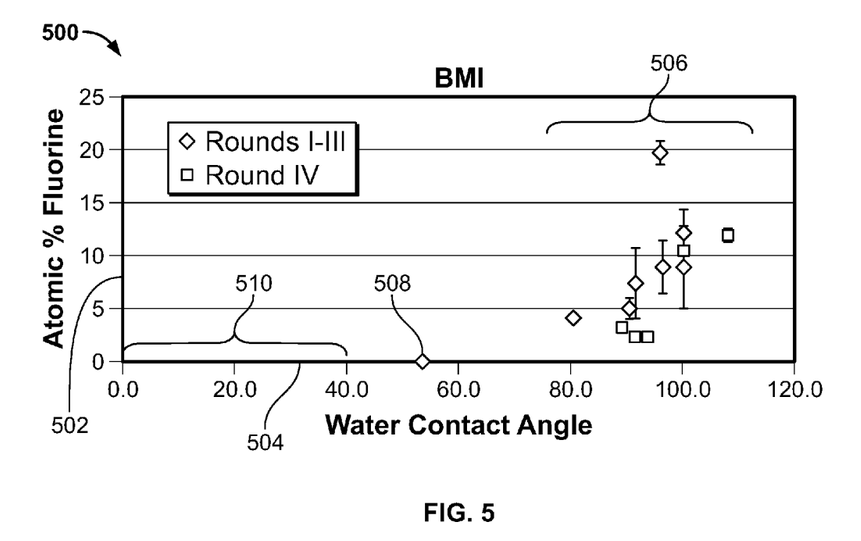
FIG. 5 is a graph relating fluorine contamination within a bismaleimide composite structure to a contact angle of a droplet deposited onto a surface of the composite structure.

FIG. 5 is a graph 500 relating fluorine contamination within a bismaleimide composite structure to a contact angle of a droplet deposited onto a surface of the composite structure. A vertical axis 502 represents an amount of atomic fluorine present within the composite bonding surfaces. A horizontal axis 504 represents the corresponding measured contact angle of water droplets. Fluorine, acting as a contaminant, may affect structural integration of the composite layers. As depicted in the graph 500, when the percentage of atomic fluorine contaminant within the composite structure increases beyond approximately 0-3%, the water contact angle increases sharply as can be seen by a grouping of points 506. A data point 508 indicates that a region 510 of the water contact angle is significantly lower with relatively lower amounts of fluorine contamination.

Figure 6:
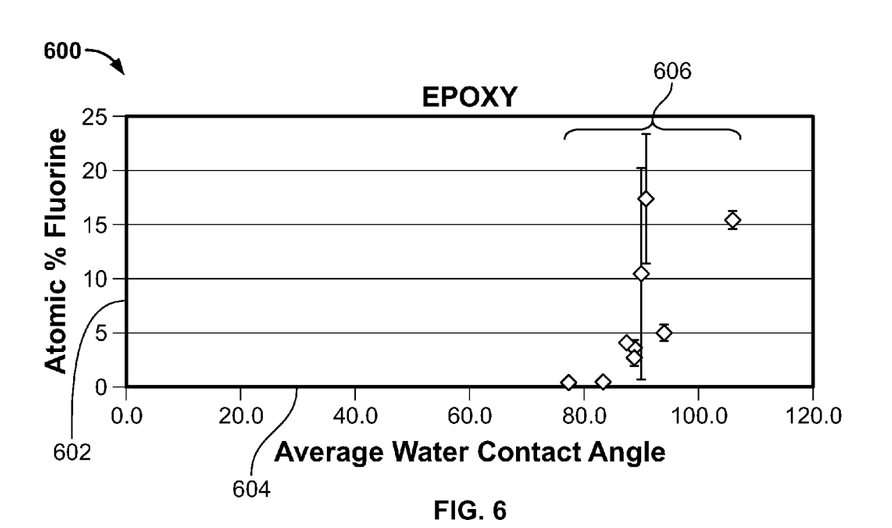
FIG. 6 is another graph relating fluorine contamination within an epoxy composite structure to a contact angle of a droplet deposited onto a surface of the composite structure.

FIG. 6 is another graph 600 relating fluorine contamination within an epoxy composite structure to a contact angle of a droplet deposited onto a surface of the composite structure. A vertical axis 602 represents an amount of atomic fluorine present within composite bonding surfaces. A horizontal axis 604 represents the corresponding measured contact angle of water droplets on the composite surface. Similar to the graph 500 of FIG. 5, a grouping 606 of relatively high water droplet contact angles is seen corresponding to composite bonding surfaces having higher fluorine content. The similarity in the groupings 506, 606 of the Graphs 500 and 600 demonstrates that the examples described herein may be applied to a variety of different composites and that the amount of contaminant present may impact structural integration of the composite bonding surfaces.

Figure 7:
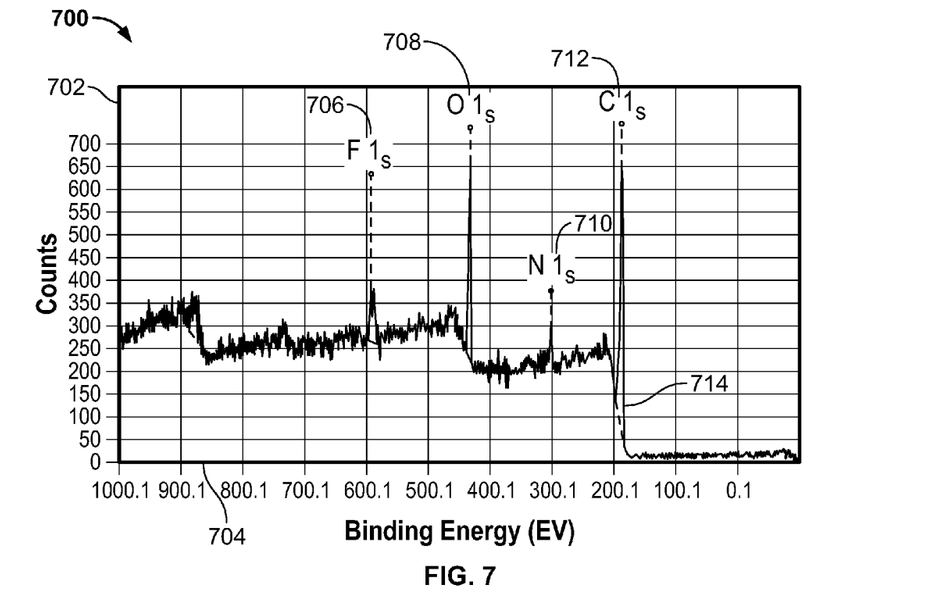
FIG. 7 is a graph relating molecular composition to binding energy after surface preparation of a composite structure.

FIG. 7 is a graph 700 relating molecular composition to binding energy (e.g., an X-ray photoelectron spectroscopy or "XPS" graph) after preparation of a composite bonding surface (e.g., after a time integral of 30 minutes on the bonding surface). A vertical axis 702 represents a count based on electron cloud counts of the molecular structures present on the composite bonding surface. A horizontal axis 704 represents the binding energy (i.e., intermolecular force) on the composite surface. Peaks 706, 708, 710, 712 indicate characteristic intermolecular contaminants that may be present between composite bonding surfaces (e.g., between the bonded layers). The peak 706 specifically corresponds to fluorine, a common contaminant present during composite layer integration. The peak 706 has a corresponding binding energy of approximately 700 electron volts (EV). The peak 708 corresponds to oxygen and has a corresponding binding energy of about 540 EV. The peak 710 corresponds to nitrogen, another contaminant that may be present and has a binding energy of approximately 400 EV. A higher contaminant binding energy corresponds to the contaminant having a greater adverse effect on the intermolecular bonding force of the composite structure. Thus, fluorine may have a greater negative impact to the intermolecular binding force than nitrogen, for example. In essence, different contaminants may have varying degrees of impact on the composite bonding structural strength. A drop off 714 is close to the peak 712, which represents carbon and corresponds to carbon being part of the composite structure.

Figure 8:
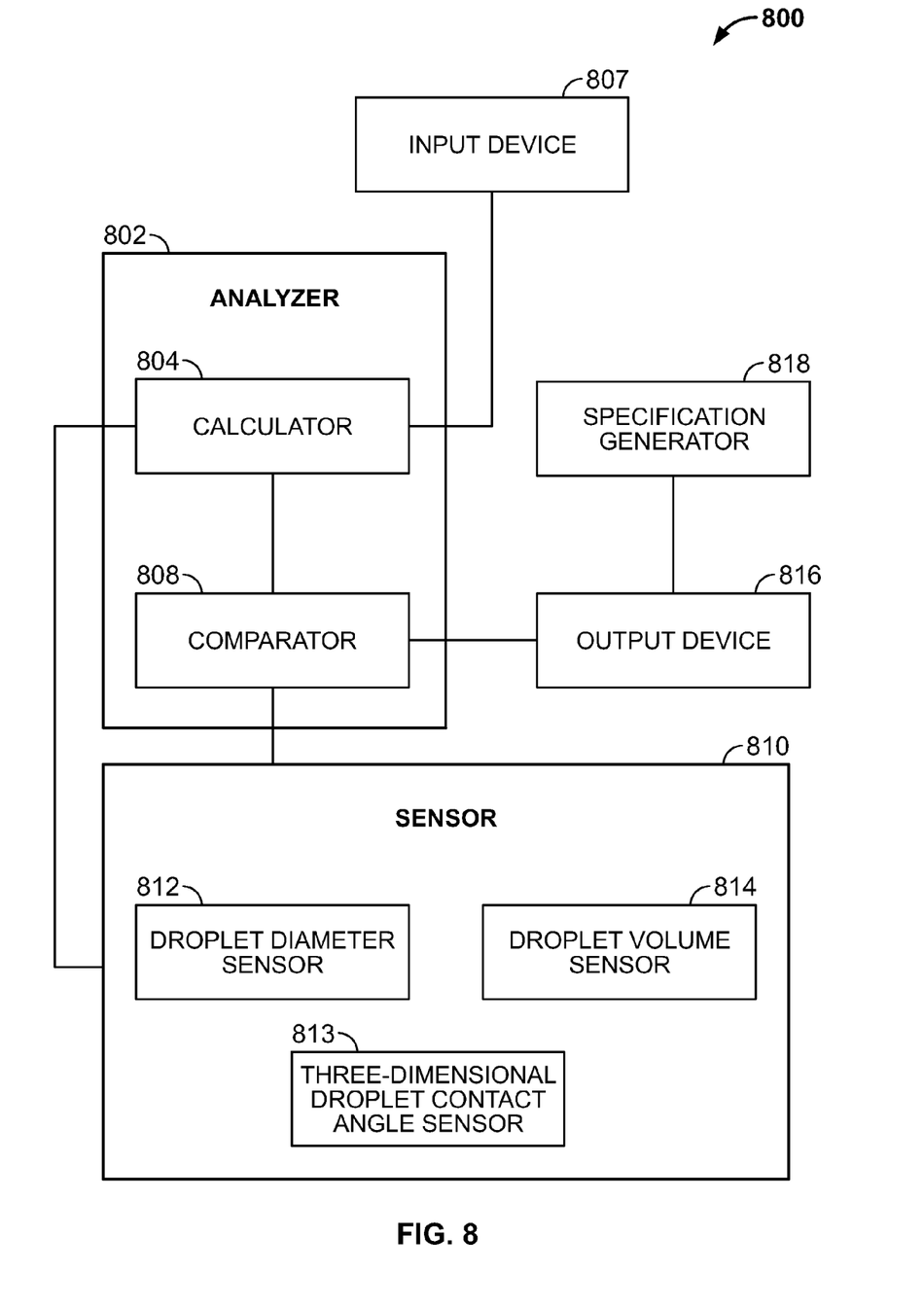
FIG. 8 is an example composite analyzing apparatus that may be used to implement the examples described.

FIG. 8 is an example composite structure analyzing apparatus 800 that may be used to implement the examples described herein. An analyzer 802 includes a calculator 804 and a comparator 808. The calculator 804 is communicatively coupled to an input device 807 (e.g., a keyboard, mouse, terminal, mobile device, etc.). The comparator 808 may, for example, be communicatively coupled to a sensor 810, which may include a droplet diameter sensor 812, a droplet three-dimensional contact angle sensor 813, and/or a droplet volume sensor 814. Alternatively, information such as droplet diameter and/or droplet volume may be manually entered through the input device 807. The comparator 808 may, for example, receive droplet three-dimensional contact angle measurements, droplet diameter measurements and/or droplet volume measurements from the sensor 810, and compare the measured three-dimensional contact angle to a pre-defined threshold angle that may be calculated by the calculator 804. The pre-defined threshold angle may be based on inputs provided to the input device 807. Additionally or alternatively, the droplet three-dimensional contact angle measurements, the droplet diameter measurements and/or the droplet volume measurements may be received from the input device 807 (e.g., provided from a user). The sensor 810 may be communicatively coupled to the calculator 804 to allow three-dimensional contact angle calculation results to be provided to the comparator 808 based on measured droplet diameter and/or droplet volume, for example. The comparator 808 may also provide comparison results between the threshold angle and the measured three-dimensional contact angle and/or calculated stresses based on the three-dimensional contact angle of the droplet to an output device 816. The output device 816 may output or display the comparison results and/or actual calculated stresses of the composite structure based on calculations at the calculator 804. Additionally or alternatively, the output device 816 may output a calculated factor of safety. The output device 816 may also trigger a specification generator 818 to generate an approval specification based on the results from the output device 816 and/or the comparator 808. In some examples, the specification generator 818 may generate an approval specification for each individual composite structure.

While an example manner of implementing the examples described herein is illustrated in FIG. 8, one or more of the elements, processes and/or devices illustrated in FIG. 8 may be combined, divided, re-arranged, omitted, eliminated and/or implemented in any other way. Further, the example analyzer 802, the example input device 807, the example sensor 810, the example output device 816, the example specification generator 818 and/or, more generally, the example composite structure analyzing apparatus 800 of FIG. 8 may be implemented by hardware, software, firmware and/or any combination of hardware, software and/or firmware. Thus, for example, any of the example analyzer 802, the example input device 807, the example sensor 810, the example output device 816, the example specification generator 818 and/or, more generally, the example composite structure analyzing apparatus 800 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example, the example analyzer 802, the example input device 807, the example sensor 810, the example output device 816, and/or the example specification generator 818 is/are hereby expressly defined to include a tangible computer readable storage device or storage disk such as a memory, a digital versatile disk (DVD), a compact disk (CD), a Blu-ray disk, etc. storing the software and/or firmware. Further still, the example composite structure analyzing apparatus 800 may include one or more elements, processes and/or devices in addition to, or instead of, those illustrated in FIG. 8, and/or may include more than one of any or all of the illustrated elements, processes and devices.

Figure 9:
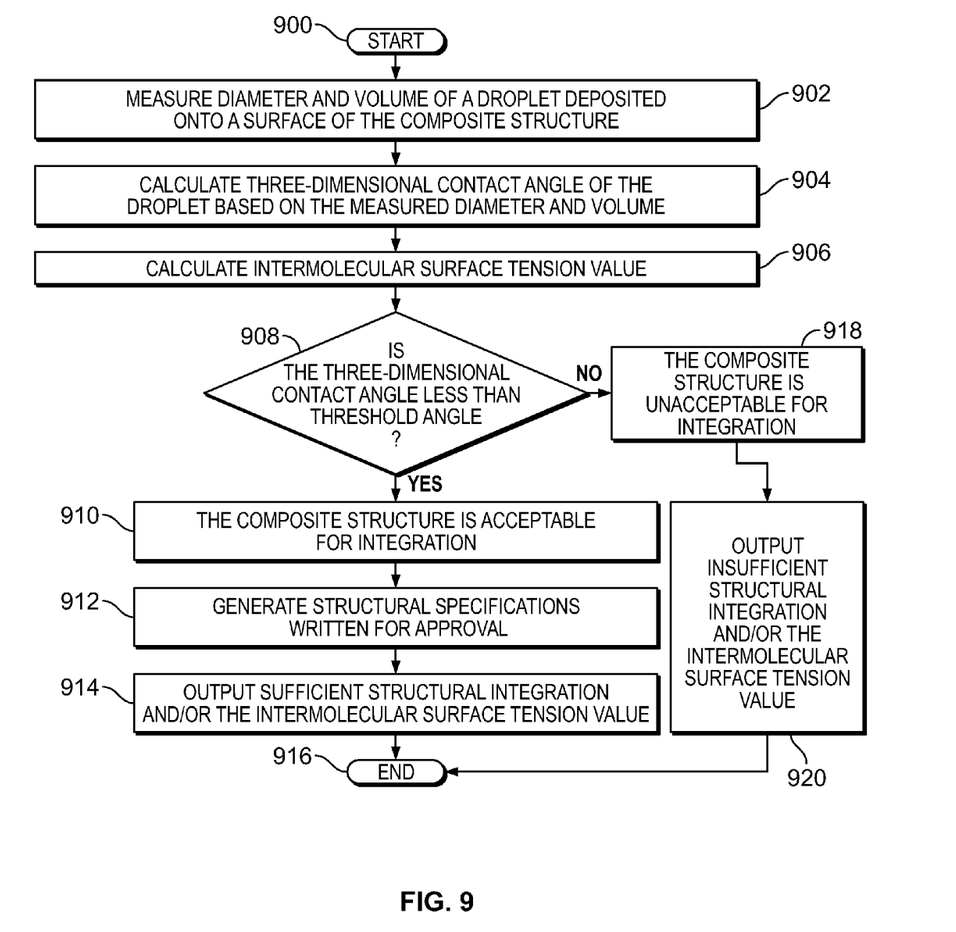
FIG. 9 is a flowchart representative of an example method that may be used to implement the composite analyzing apparatus of FIG. 8.

A flowchart representative of an example method that may be used to implement the composite structure analyzing apparatus 800 is shown in FIG. 9. In this example, the method may be implemented using machine readable instructions that comprise a program for execution by a processor such as the processor 1012 shown in the example processor platform 1000 discussed below in connection with FIG. 10. The program may be embodied in software stored on a tangible computer readable storage medium such as a CD-ROM, a floppy disk, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowchart illustrated in FIG. 9, many other methods of implementing the example composite structure analyzing apparatus 800 may alternatively be used. For example, the order of execution of the blocks may be changed, and/or some of the blocks described may be changed, eliminated, or combined.

The example method of FIG. 9 is described below in connection with the composite structure analyzing apparatus 800 of FIG. 8. The example method of FIG. 9 begins at block 900 where composite layers are gathered and prepared (e.g., formed) by bonding the composite layers by using, for example, adhesive (block 900). A diameter and/or volume of a droplet deposited onto a surface of the composite structure is measured (block 902). A three-dimensional contact angle of the droplet is then calculated (block 904) using, for example, Equation 2 in conjunction with the measured diameter and/or the measured volume of the droplet. The three-dimensional contact angle may be calculated using the Bikerman equation (i.e., Equation 2), for example. Although measured diameters and measured volumes are described, any other appropriate variables may be used to determine the three-dimensional contact angle. Alternatively, the three-dimensional contact angle may be measured. The three-dimensional contact angle of the droplet allows an intermolecular surface tension value to be calculated by, for example, a modified Young's equation such as Equation 1 (block 906). The three-dimensional contact angle is then compared to the threshold angle (block 908). The three-dimensional contact angle being less than the threshold angle indicates sufficient structural integration of the composite structure and that the composite structure is acceptable for integration (block 910) and structural specifications written for approval may be generated (block 912). Accordingly, an output message indicating sufficient structural integration and/or displaying an intermolecular surface tension value may be generated and/or displayed (block 914) and the process may end (block 916). The output message may also include a factor of safety based on the intermolecular surface tension based of the composite structure. Alternatively, the three-dimensional contact angle of the droplet being greater than the threshold angle (block 908) indicates the composite structure does not have sufficient structural integration and may be deemed unacceptable for product integration (block 918). Accordingly, an output message indicating insufficient structural integration and/or displaying an intermolecular surface tension value (block 920) may be generated, and the process may end (block 916).

As mentioned above, the example processes of FIG. 9 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 9 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 10:
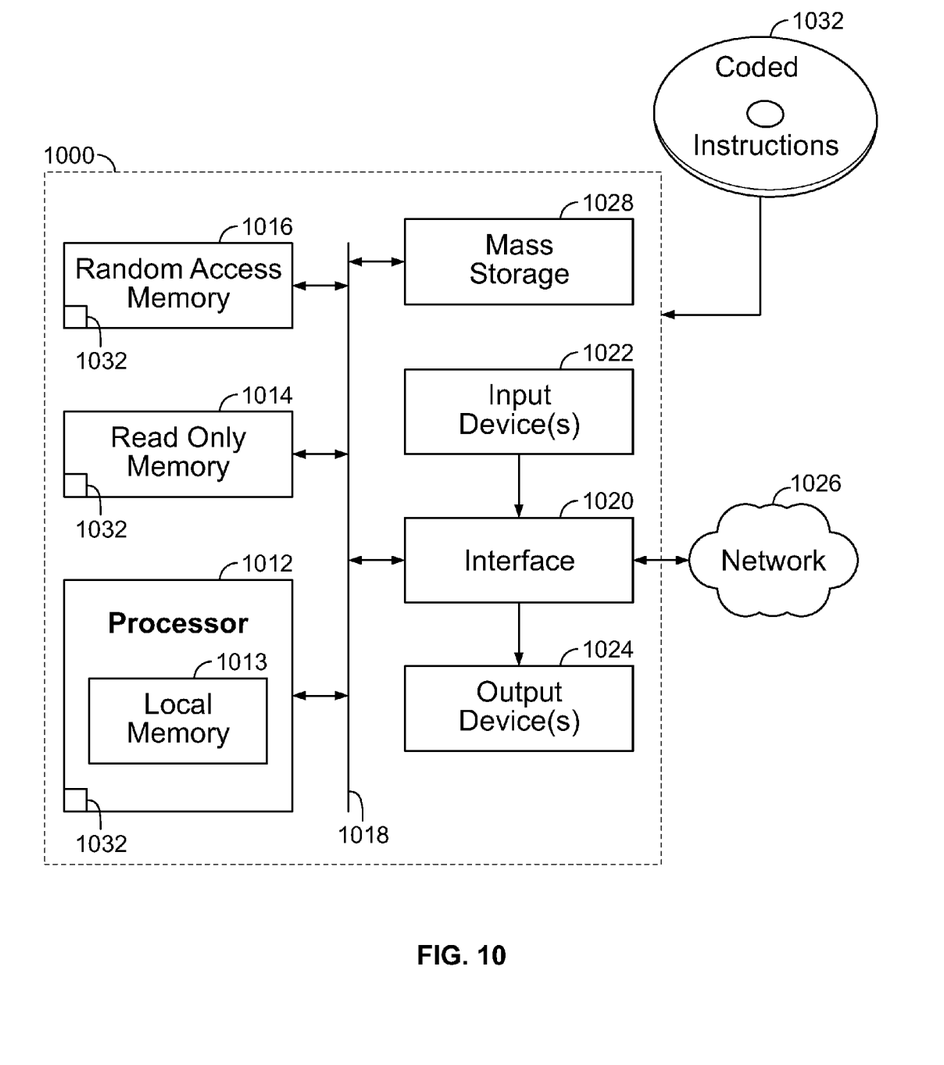
FIG. 10 is a block diagram of an example processor platform capable of executing machine readable instructions to implement the method of FIG. 9.

FIG. 10 is a block diagram of an example processor platform capable of executing the instructions of FIG. 9 to implement the composite structure analyzing apparatus 800 of FIG. 8. The processor platform 1000 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors or controllers from any desired family or manufacturer.

The processor 1012 of the illustrated example includes a local memory 1013 (e.g., a cache). The processor 1012 of the illustrated example is in communication with a main memory including a volatile memory 1014 and a non-volatile memory 1016 via a bus 1018. The volatile memory 1014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 may be implemented by flash memory and/or any other desired type of memory device. Access to the main memory 1014, 1016 is controlled by a memory controller.

The processor platform 1000 of the illustrated example also includes an interface circuit 1020. The interface circuit 1020 may be implemented by any type of interface standard, such as an Ethernet interface, a universal serial bus (USB), and/or a PCI express interface.

In the illustrated example, one or more input devices 1022 are connected to the interface circuit 1020. The input device(s) 1022 permit a user to enter data and commands into the processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1020 of the illustrated example, thus, typically includes a graphics driver card.

The interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

Coded instructions 1032 to implement the methods described herein may be stored in the mass storage device 1028, in the volatile memory 1014, in the non-volatile memory 1016, and/or on a removable tangible computer readable storage medium such as a CD or DVD.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent. While aircraft are described, the example apparatus may be applied to vehicles, aerodynamic structures, etc.

What is claimed is:

1. A method for determining a bond strength of a composite structure for an aircraft, the method comprising:
    applying a fluid droplet to a surface of the composite structure;
    determining a three-dimensional contact angle between the surface and a portion of the droplet;
    comparing the three-dimensional contact angle to a threshold angle; and
    determining whether the bond strength is sufficient based on the comparison, wherein a value of the three-dimensional contact angle of less than a predetermined threshold angle of about 10 degrees between the surface of the composite structure and the portion of the fluid droplet is indicative of the composite structure having sufficient bond strength to provide a pre-predetermined load bearing capacity.

2. The method as defined in claim 1, further comprising selecting the composite structure for integration into an assembly when the bond strength is sufficient.

3. The method as defined in claim 1, further comprising approving the composite structure when the bond strength is sufficient after integration of the composite structure into an assembly.

4. The method as defined in claim 1, wherein the three-dimensional contact angle being less than the threshold angle indicates sufficient bond strength of the composite structure.

5. The method as defined in claim 1, wherein the three-dimensional contact angle being greater than the threshold angle indicates insufficient bond strength of the composite structure.

6. The method as defined in claim 1, wherein determining the three-dimensional contact angle further comprises measuring a diameter and volume of the droplet.

7. The method as defined in claim 1, wherein the portion of the droplet comprises a head or a tail of the droplet.

8. The method as defined claim 7, wherein the composite structure comprises bismaleimide, epoxy, polyamide, or thermoplastic.

9. The method as defined in claim 1, wherein the threshold angle is calculated based on a pre-determined load bearing capacity.

10. The method as defined in claim 9, wherein the threshold angle calculation is calculated using an equation including a component of the surface tension of the surface due to vapor gaseous phase of the droplet in equilibrium.

11. The method as defined in claim 1, wherein applying the fluid droplet comprises use of a pipette or ballistic deposition.

12. An aircraft component that requires fewer fasteners, comprising:
    an external skin having a bonded composite structure, defining a skin surface area of an aircraft;
    a support frame; and
    an adhesive applied to the composite structure to attach the external skin to the support frame,
    wherein the composite structure has sufficient bond strength to enable adhesive attachment of the external skin to the support frame with less than 0.50 fasteners to couple the skin and the support frame per square-foot of the skin surface area, where a three-dimensional contact angle between the composite structure and a portion of a fluid droplet applied to the surface of the composite structure is less than a pre-determined threshold angle of about 10 degrees is indicative of sufficient bond strength.

13. The apparatus as defined in claim 12, wherein the composite structure is outboard of an aircraft.

14. The apparatus as defined in claim 12, wherein the portion of the fluid droplet defining the three-dimensional contact angle from the composite structure comprises one or more of a head, a tail, or a mid-section of a loft of the droplet.

15. A tangible machine readable medium having instructions stored thereon, which when executed, cause a machine to:
   determine a three-dimensional contact angle of a droplet placed onto a surface of a composite structure based on a measured diameter and volume of the droplet;
   compare the three-dimensional contact angle to a threshold angle of about 10 degrees,
   wherein the three-dimensional contact angle being less than the threshold angle indicates sufficient bond strength of the composite structure, and
   wherein the three-dimensional contact angle being greater than the threshold angle indicates insufficient bond strength of the composite structure; and
   output whether the composite structure has sufficient bond strength.

16. The machine readable medium as defined in claim 15, which when executed, further cause a machine to measure the volume and the diameter of the droplet.

17. The machine readable medium as defined in claim 15, which when executed, further cause a machine to calculate an intermolecular surface tension of the composite structure.

18. The machine readable medium as defined in claim 17, wherein the calculated intermolecular surface tension is determined using an equation including a component of the surface tension of the surface due to vapor gaseous phase of the droplet in equilibrium.

19. The machine readable medium as defined in claim 17, which when executed, further cause a machine to output one or more of the intermolecular surface tension and a factor of safety based on the intermolecular surface tension.

20. The machine readable medium as defined in claim 15, which when executed, further cause a machine to generate structural specifications for approval when the three-dimensional contact angle indicates sufficient bond strength.

\* \* \* \* \*

UNITED STATES PATENT AND TRADEMARK OFFICE
CERTIFICATE OF CORRECTION

PATENT NO.        : 9,518,907 B2
APPLICATION NO.   : 14/157211
DATED             : December 13, 2016
INVENTOR(S)       : Eugene A. Dan-Jumbo It is certified that error appears in the above-identified patent and that said Letters Patent is hereby corrected as shown below:

In the Claims

Column 12, Line 34 (Claim 8): Add --in-- after "defined"

Signed and Sealed this
Twenty-eighth Day of February, 2017

Michelle K. Lee
*Director of the United States Patent and Trademark Office*